United States Patent
Schoeler et al.

(10) Patent No.: US 12,332,424 B2
(45) Date of Patent: Jun. 17, 2025

(54) HOLDER FOR AN OPTICAL SYSTEM OF AN ENDOSCOPE AND METHOD FOR MANUFACTURING A HOLDER FOR AN OPTICAL SYSTEM OF AN ENDOSCOPE

(71) Applicant: OLYMPUS WINTER & IBE GMBH, Hamburg (DE)

(72) Inventors: Uwe Schoeler, Hoisdorf (DE); Nils Torkuhl, Gross Vollstedt (DE); Martin Wieters, Barsbuettel (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 941 days.

(21) Appl. No.: 17/020,073

(22) Filed: Sep. 14, 2020

(65) Prior Publication Data
US 2020/0409136 A1 Dec. 31, 2020

Related U.S. Application Data

(63) Continuation of application No. PCT/EP2019/055404, filed on Mar. 5, 2019.

(30) Foreign Application Priority Data

Mar. 14, 2018 (DE) .......................... 102018105845.4

(51) Int. Cl.
*G02B 23/24* (2006.01)
*A61B 1/00* (2006.01)
(Continued)

(52) U.S. Cl.
CPC ..... *G02B 23/2476* (2013.01); *G02B 23/2415* (2013.01); *G02B 23/2423* (2013.01);
(Continued)

(58) Field of Classification Search
CPC ............ G02B 23/2476; G02B 23/2415; G02B 23/2423; H04N 13/239; A61B 1/00096;
(Continued)

(56) References Cited

U.S. PATENT DOCUMENTS 6,767,322 B1 * 7/2004 Futatsugi ........... A61B 1/00096
600/129
2005/0192477 A1 9/2005 Forster et al.
(Continued)

FOREIGN PATENT DOCUMENTS

DE 19941320 A1 3/2000
DE 102004009383 A1 9/2005
(Continued)

OTHER PUBLICATIONS

International Search Report dated May 24, 2019 issued in PCT/EP2019/055404.

*Primary Examiner* — William R Alexander
*Assistant Examiner* — Mackenzi Waddell
(74) *Attorney, Agent, or Firm* — Scully, Scott, Murphy & Presser, P.C.

(57) ABSTRACT

A holder for an optical system of an endoscope, the holder including: a take-up region configured to receive an optical element; and at least one fixing region configured to fix the holder in the optical system by a soldered connection, the fixing region being separate from the take-up region; wherein a material of the holder is a base material that is provided with a coating, a material of the coating having better solderability than the base material, the coating being removed from the take-up region to expose a surface of the take-up region, the exposed surface being blackened by a laser-assisted surface treatment.

20 Claims, 4 Drawing Sheets

(51) Int. Cl.
*A61B 1/05* (2006.01)
*H04N 13/239* (2018.01)

(52) U.S. Cl.
CPC ........ *H04N 13/239* (2018.05); *A61B 1/00096* (2013.01); *A61B 1/0011* (2013.01); *A61B 1/00193* (2013.01); *A61B 1/051* (2013.01)

(58) Field of Classification Search
CPC .... A61B 1/0011; A61B 1/00193; A61B 1/051
See application file for complete search history.

(56) References Cited

U.S. PATENT DOCUMENTS

| | | | |
|---|---|---|---|
| 2008/0151041 A1 | | 6/2008 | Shafer et al. |
| 2013/0085328 A1 | | 4/2013 | Kitano |
| 2014/0288370 A1 | * | 9/2014 | Jungbaer ............ A61B 1/00096 |
| | | | 600/112 |
| 2015/0136226 A1 | | 5/2015 | Guo et al. |
| 2018/0360298 A1 | * | 12/2018 | Khettal .............. A61B 1/00179 |
| 2020/0387007 A1 | * | 12/2020 | Mizuta ..................... A61B 3/12 |

FOREIGN PATENT DOCUMENTS

| | | | | |
|---|---|---|---|---|
| DE | 102007046609 A1 | | 4/2008 | |
| DE | 102013016316 A1 | | 4/2015 | |
| EP | 1455216 A1 | | 9/2004 | |
| JP | H09-265047 A | | 10/1997 | |
| JP | 2000-010022 A | | 1/2000 | |
| JP | 2000-342512 A | | 12/2000 | |
| JP | 2002-336190 A | | 11/2002 | |
| WO | WO-2016030008 A1 | * | 3/2016 | ......... A61B 1/00096 |
| WO | WO-2016207659 A1 | * | 12/2016 | ......... B23K 26/0006 |
| WO | WO 2018/024548 A1 | | 2/2018 | |

\* cited by examiner

HOLDER FOR AN OPTICAL SYSTEM OF AN ENDOSCOPE AND METHOD FOR MANUFACTURING A HOLDER FOR AN OPTICAL SYSTEM OF AN ENDOSCOPE

CROSS-REFERENCE TO RELATED APPLICATION

The present application is a continuation of PCT/EP2019/055404 filed on Mar. 5, 2019, which is based upon and claims the benefit to DE 10 2018 105 845.4 filed on Mar. 14, 2018, the entire contents of each of which are incorporated herein by reference.

BACKGROUND

Field

The present disclosure relates to a holder for an optical system of an endoscope, comprising a take-up region, configured to receive an optical element, and at least one fixing region, which is configured to fix the holder in the optical system by means of a soldered connection and is separate from the take-up region. In addition, the present disclosure relates to an optical system for an endoscope, to an endoscope and to a method for manufacturing a holder for an optical system of an endoscope.

Prior Art

With medical endoscopes, a small outside diameter of the endoscope shaft is desirable. Due to increasing miniaturization, the production and assembly of the optical system constitute a technical challenge. Thus, it has to be guaranteed, for example, during the miniaturization of the optical system that the optical properties of the endoscope comply with the specifications and the endoscope simultaneously withstands the stresses to which it is exposed during operation and during preparation. This applies to the holders in the optical system, which can receive components such as, for example, optical elements and image sensors.

Stereo-video endoscopes have two lens system channels which are separate from one another and which, in each case, image light bundles from a field of view having a slightly different viewing angle in each case on an image sensor. In this way, a stereo image of the take-up region can be composed, which provides an observer with a spatial impression. The use of two lens system channels requires a space-saving design of the optical system, so as not to unnecessarily enlarge the outside diameter of the stereo-video endoscope.

SUMMARY

It is an object to indicate a holder for an optical system of an endoscope, an optical system for an endoscope, an endoscope and a method for manufacturing a holder for an optical system of an endoscope, wherein the holder is intended to make possible a stable and reliable construction with a small installation space.

Such object can be solved by a holder for an optical system of an endoscope, comprising a take-up region, configured to receive an optical element, and at least one fixing region, which is configured to fix the holder in the optical system by a soldered connection and is separate from the take-up region, wherein a material of the holder is a base material that is provided with a coating, the material of the coating having better solderability than the base material, and the coating in the take-up region being removed and the surface of the take-up region being blackened by means of laser-assisted surface treatment.

In the context of the present specification, a distal optical assembly denotes an optical assembly which lies distally of the proximal optical assembly which is likewise mentioned. The same applies to the proximal optical assembly.

Thanks to such holder, it is possible to reliably solder in the optical system, since the holder is provided in the fixing region with a coating which can be soldered well. On the other hand, a loss in the quality of the imaging properties due to reflections of incident light bundles in the take-up region of the optical element is avoided by blackening the take-up region.

Holders in the optical system of an endoscope have to be manufactured precisely and have to have a high durability. In addition, the thermal expansion coefficient of the material of the holder must not differ too significantly from the thermal expansion coefficient of the materials of a received optical element, that is to say, for example, glass, silicon and ceramic. The base material is a material of the holder, which can be blacked by the action of a laser beam. The base material can be a metal, for example a steel alloy.

A material having good solderability can be used as the material for the coating such as, for example, gold, silver, tin or palladium. Since these materials have considerably better solderability than, for example, a steel alloy, the fixing region of the holder can be reliably and stably connected to a corresponding fixing element of the optical system by means of a soldered connection. The coating can be electroplated. However, other types of the coating, with which a thin layer can be applied, are equally provided. For example, the coating can be vapor-deposited. During the coating process, the material deployed for the coating can be applied to a large part of the entire surface of the holder. However, the materials used for the coating have, in many cases, a high reflectance at least in parts of the wavelength range of the visible light. The result of this is that, in the take-up region which may be likewise coated initially, reflections of incident light bundles off the coated surfaces can occur. This would decrease the optical quality of the optical system.

In order to avoid this unwanted effect only the fixing region of the holder can be coated. Such a targeted partial coating of only the fixing region is, however, technically complex. An initial coating of the take-up region can be accepted and the coating which is not wanted at this point can be subsequently removed again by means of laser-assisted surface treatment.

In addition, the surface of the holder in the take-up region can be blackened by means of the laser-assisted surface treatment performed. Thus, reflections in the take-up region can be further reduced, compared with an untreated surface of the base material. During such laser-assisted surface treatment, the machined region can be restricted very precisely so that only the take-up region is machined.

Laser-assisted surface treatment in the context of the present specification refers to a machining of a surface of a material by means of a laser beam as is known, for example, from laser ablation and laser marking. The term "laser-assisted surface treatment" thus includes both the removal of material (laser ablation) and the modification of the surface as occurs during laser marking, with the objective of blackening.

The base material from which the holder is produced can be a steel alloy, such as chrome steel. Chrome steel has the required durability, and the desired ductility and can, in addition, be blackened well and efficiently by means of laser-assisted surface treatment. A chrome steel having the material number 1.4104 or 1.4021 can be deployed. However, other steel alloys or other materials can also be deployed, which can be blackened by means of laser-assisted surface treatment.

The coating can be removed in the take-up region and the surface of the take-up region can be blackened by laser-assisted surface treatment with an ultrashort-pulse laser. An ultrashort-pulse laser is, for example, a picosecond laser or a femtosecond laser. The use of an ultrashort-pulse laser can be used, since the coating can be efficiently removed and the surface can be efficiently blackened.

According to a further embodiment, the optical element, which the take-up region is configured to receive, can be an optical deflection element, such as a deflection prism. The propagation direction of a bundle of rays incident into the optical deflection element can be modified by means of an optical deflection element. A deflection prism is an example of such an optical deflection element. By blackening the take-up region, reflections off the take-up region of the optical deflection element, which would deteriorate the image quality of the endoscope, can be reduced or prevented.

According to a further embodiment, the holder can be configured to receive an image sensor in such a manner that a light-sensitive sensor surface of the received image sensor extends parallel to a direction of incident light, wherein light bundles incident along the direction of incident light into the optical deflection element are deflected in the direction of the received image sensor by the optical deflection element.

The direction of incident light can correspond to an optical axis of the optical system. By receiving an image sensor, the active surface of which extends parallel to the direction of incident light, a space-saving arrangement of the image sensor in the optical system can be achieved. According to this embodiment, the holder can be configured to receive both the image sensor and the optical deflection element.

Such object can be, in addition, solved by an optical system for an endoscope, comprising at least one holder according to one or more of the previously described embodiments and at least one optical element, wherein the optical element is received in the take-up region of the holder and the holder is fixed in the optical system by means of at least one soldered connection, wherein the soldered connection connects the fixing region of the holder to a fixing element of the optical system.

The optical element can be fixed in the take-up region of the holder by means of a bonding method.

The optical system has the same or similar advantages as the holder. A compact, stable and high-quality optical system is provided.

The holder can have a first fixing region and a second fixing region, wherein the first fixing region is connected by means of a first soldered connection to a first fixing element and the second fixing region is connected by means of a second soldered connection to a second fixing element. The holder is thus fixed in the optical system by means of two soldered connections. This can increase the stability of the optical system.

According to an embodiment, the optical system can be configured for use in a stereo-video endoscope, wherein the optical system comprises a first lens system channel having a first optical axis and a second lens system channel having a second optical axis, wherein the first optical axis runs parallel to the second optical axis, wherein the optical system comprises a first holder and a second holder which are configured in accordance with the holder, and a first optical element is received in the take-up region of the first holder and a second optical element is received in the take-up region of the second holder, wherein the optical system is configured in that that light bundles guided along the first lens system channel are diverted by the first optical element and light bundles guided along the second lens system channel are diverted by the second optical element. According to this embodiment, a holder having an optical element is consequently provided for each lens system channel of the optical system.

The optical system can be an optical system of a stereo-video endoscope. The terms "distal optical assembly" and "proximal optical assembly" are understood, in the context of the present description and in the context of a stereo-video endoscope, to mean that both the distal and the proximal optical assembly are a part of an assembly in which the two optical channels (left channel and right channel) are guided separately.

Thanks to the holders, a space-saving and stable construction is realized with low manufacturing outlay and good optical properties. The first and the second holder can each be configured as described above with respect to the holder such that the first and the second holder have an identical design.

The first holder and the second holder can be arranged symmetrically to one another in the optical system, wherein the first holder can be arranged axisymmetrically to the second holder with respect to a longitudinal axis of the optical system, wherein the longitudinal axis runs centrally between the first optical axis and the second optical axis. Thanks to the symmetrical arrangement of the holders, the optical system can become even more space-saving and durable.

According to a further embodiment, each holder can be configured to receive an image sensor, wherein the active surfaces of the image sensors are in each case arranged parallel to the lens system channels, and wherein the first optical element and the second optical element are optical deflection elements, such as deflection prisms, which are configured to deflect light bundles incident into the optical deflection elements in the direction of the image sensors.

Such object can be, in addition, solved by an endoscope, such as a stereo-video endoscope, comprising an optical system according to one of the previously described embodiments.

The endoscope also has the same or similar advantages to the holder and the optical system.

Such object can be additionally solved by a method for manufacturing a holder for an optical system of an endoscope, having the following method steps which are to be carried out successively:
  providing a blank of the holder made from a base material,
  coating the blank with a coating, the coating having better solderability than the base material, wherein a fixing region for fixing in the optical system is provided on the coated blank by means of a soldered connection,
  treating a take-up region of the coated blank with a laser, wherein the take-up region is configured to receive an optical element and is separate from the fixing region, and wherein the coating in the take-up region is removed and the surface of the take-up region is blackened by the laser treatment.

Thus, a precise and efficient method for manufacturing a holder for an optical system of an endoscope is provided.

The laser treatment of the take-up region can be effected with an ultrashort-pulse laser.

Furthermore, the removal of the coating in the take-up region and the blackening of the take-up region can be effected with a single laser source, wherein the removal of the coating in the take-up region and the blackening of the take-up region can be performed in a single work step. As a result, the outlay during the production and the production costs can be reduced.

Such object can be solved by a holder, produced with the previously described method.

BRIEF DESCRIPTION OF THE DRAWINGS

Further features will become evident from the description of embodiments, together with the claims and the appended drawings. Embodiments can fulfill individual features or a combination of multiple features.

The embodiments will be described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals so that they are not introduced again in each case.

DETAILED DESCRIPTION

Figure 1:
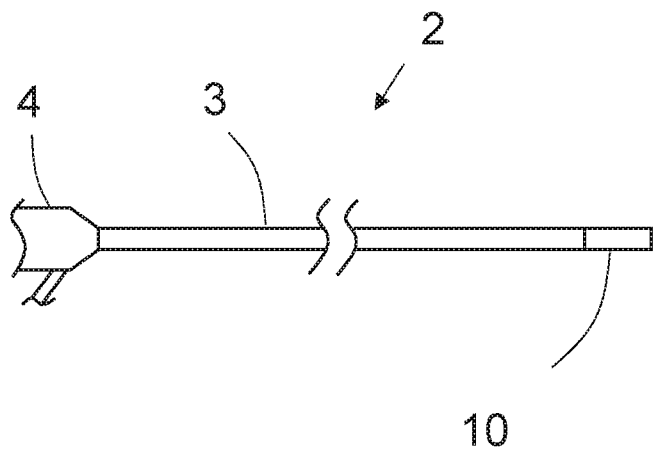
FIG. 1 illustrates a schematic representation in sections of an endoscope.

FIG. 1 shows in a schematic and simplified manner an endoscope 2 having a shaft 3 and a handle 4, which is shown in sections. The endoscope 2 is, for example, a video endoscope, additionally for example a stereo-video endoscope. An optical system 10 is situated at a distal end of the shaft 3.

Figure 2:
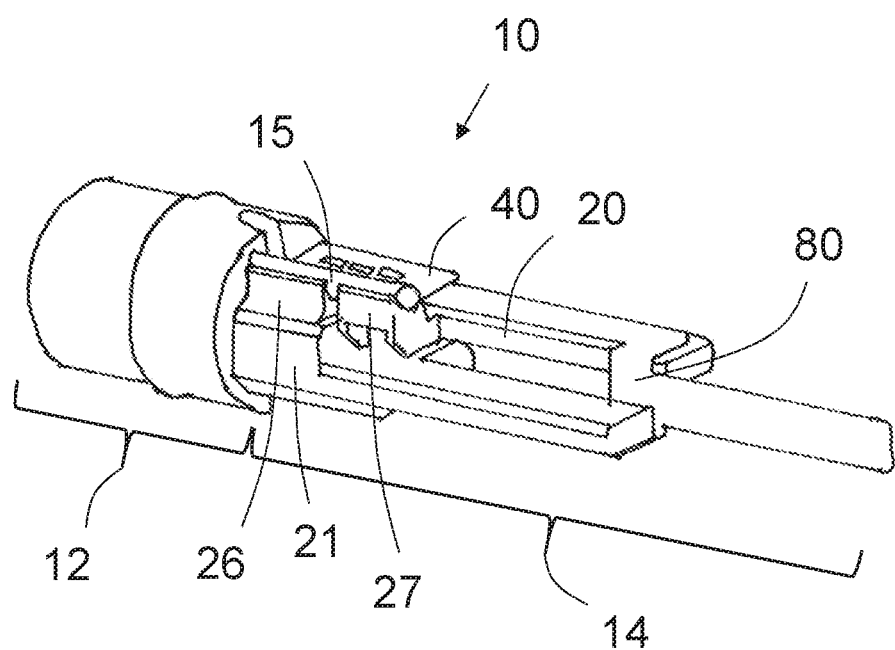
FIG. 2 illustrates a schematically simplified representation of an optical system for a stereo-video endoscope having two holders.

Such an optical system 10 for a stereo-video endoscope is shown in FIG. 2 in a schematically simplified perspective representation. The optical system 10 comprises a distal optical assembly 12 and a proximal optical assembly 14. The optical system 10, that is to say the distal optical assembly 12 and the proximal optical assembly 14, is situated in a part or portion of the entire optical system of the stereo-video endoscope, in which the two optical channels (left channel and right channel) are guided separately.

A number of optical elements, which are not depicted in FIG. 2, are arranged in the distal optical assembly 12. Light bundles incident from a treatment and/or observation space at a distal tip of the shaft 3 are received by the distal optical assembly 12 and forwarded to the proximal optical assembly 14. The proximal optical assembly 14 comprises two image sensors 40, merely one of which is visible in FIG. 2. The image sensors 40 are coupled to (for example, flexible) printed circuit boards 80 for forwarding image signals in the direction of the handle 4, for example mounted on the relevant printed circuit boards 80.

The embodiment of the optical system 10, which is shown in FIG. 2, comprises a proximal optical assembly 14 having a first holder 20 and a second holder 21 which are configured to receive the image sensors 40. In order to fix the proximal optical assembly 14 on the distal optical assembly 12, the first holder 20 and the second holder 21 each have a first fixing region 26 and a second fixing region 27. The fixing regions 26, 27 are configured to receive a cylindrical fixing element 15.

In the display selected in FIG. 2, merely the first fixing region 26 of the second holder 21 and the second fixing region 27 of the first holder 20 are visible, which are soldered to a first fixing element 15. The second fixing element 16 is hidden in FIG. 2. The fixing elements 15, 16 are fastened to the distal optical assembly 12 and are, in each case, fixed to the first fixing region 26 of a holder 20, 21 and to the second fixing region 27 of the other holder 20, 21 with a soldered connection. In this way, a very stable and space-saving arrangement of the holders 20, 21 is achieved.

Figure 3:
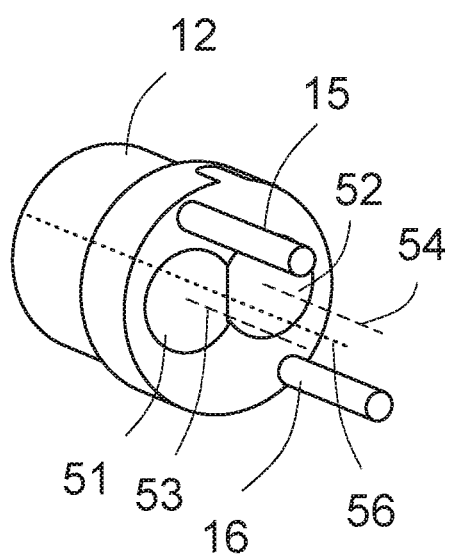
FIG. 3 illustrates a schematically simplified representation of a distal assembly of an optical system for a stereo-video endoscope having two fixing elements.

FIG. 3 shows a schematically simplified representation of the distal optical assembly 12, in which the two fixing elements 15, 16 can be seen. In addition, a first lens system channel 51 having a first optical axis 53 and a second lens system channel 52 having a second optical axis 54 are depicted. A longitudinal axis 56 of the optical assembly 12 extends centrally between the two optical axes 53, 54. The first fixing element 15 is arranged above and the second fixing element 16 is arranged below the lens system channels 51, 52.

Figure 4:
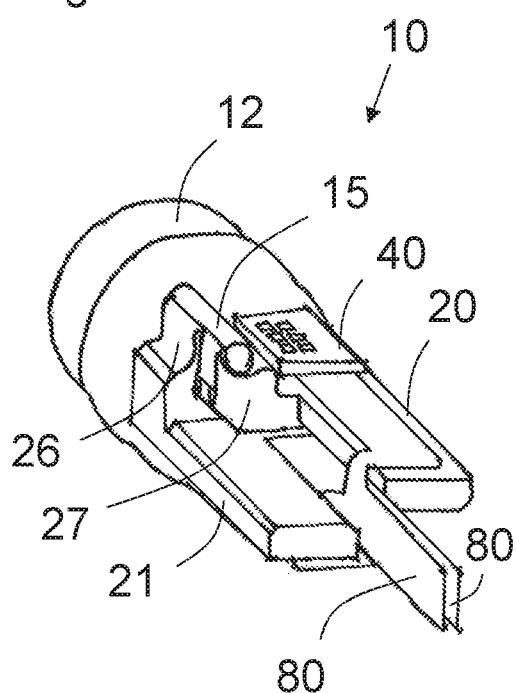
FIG. 4 illustrates a schematically simplified representation of an optical system for a stereo-video endoscope having two holders in a view which is rotated with respect to the representation in FIG. 3.

A further schematically simplified perspective display of the optical system 10 is shown in FIG. 4. It can be seen in this representation that a printed circuit board 80 is in each case connected to an image sensor 40. Since the image sensors 40 are arranged parallel to the longitudinal axis 56, deflection prisms are arranged in the holders 20, 21, which are hidden in FIGS. 2 to 4. The deflection prisms deflect the light bundles incident along the optical axes 53, 54 in the direction of the image sensors 40.

Figure 5:
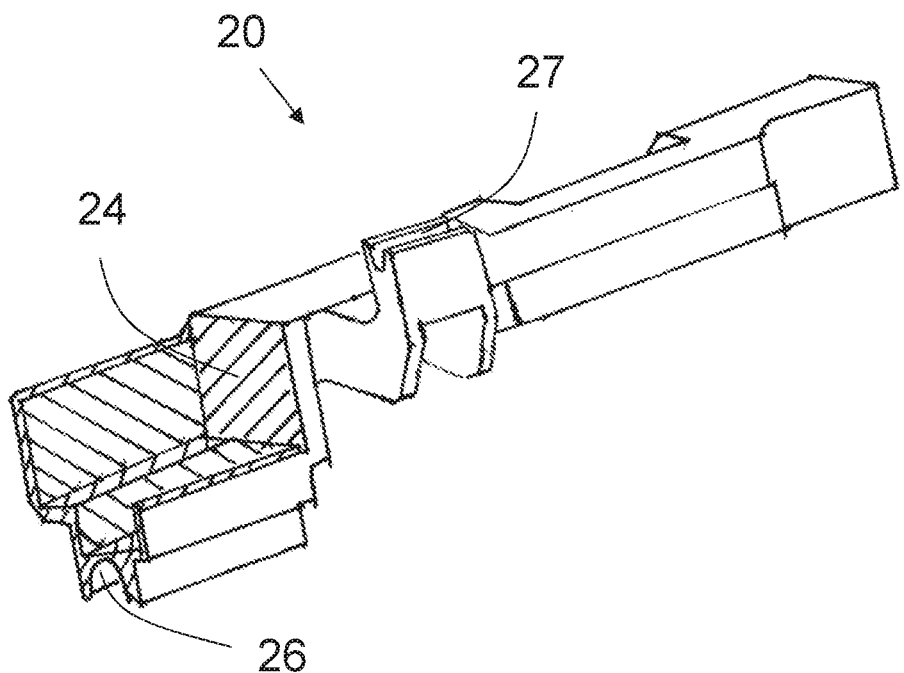
FIG. 5 illustrates a schematically simplified perspective representation of a holder for an optical system of an endoscope.

FIG. 5 shows a schematically simplified perspective representation of a holder 20. In this display, the fixing regions 26, 27 can be seen, with which the holder 20 is fixed in the optical system 10 to the fixing elements 15, 16. Furthermore, FIG. 5 shows the take-up region 24 which is depicted in a hatched manner, which is configured to receive an optical element. If the image sensors 40 are arranged parallel to the longitudinal axis 56, as shown for example in FIGS. 2 to 4, a deflection prism which deflects light bundles incident along the optical axes 53, 54 in the direction of the image sensors 40 is used, for example, as an optical element.

In order to guarantee the stability of the holder 20, the latter must be manufactured from a stable and ductile material that, in addition, has a similar thermal expansion coefficient to the materials of the optical element. To ensure that the soldered connection between the fixing regions 26, 27 and the fixing elements 15, 16 is durable, the fixing regions 26, 27 must in addition have high solderability. Finally, no reflections are to occur in the take-up region 24, since these have a negative effect on the image quality of the endoscope 2.

Figure 6A:
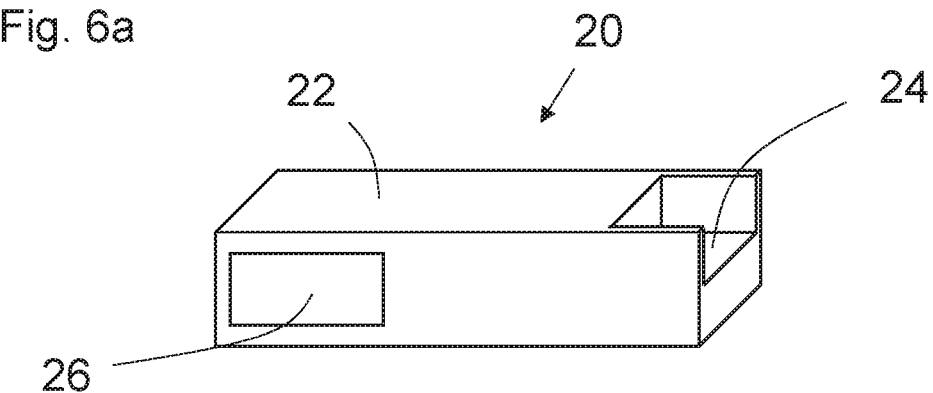
FIGS. 6a to 6c illustrate a schematic representation of a method for manufacturing a holder for an optical system of an endoscope.
Figure 6B:
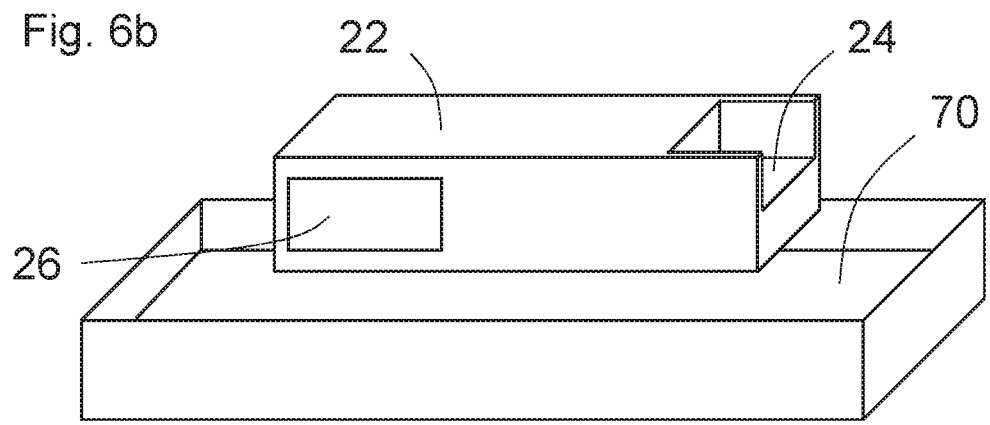
Figure 6C:
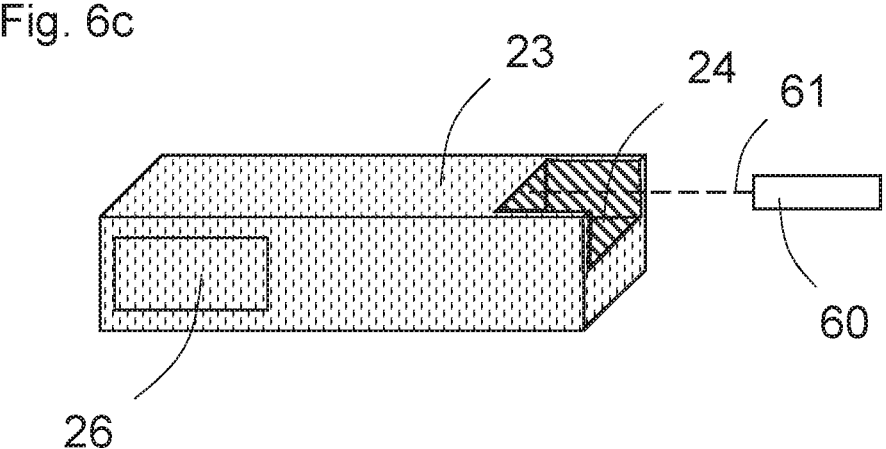

In order to meet all of these requirements, a method, which is schematically described in FIGS. 6a to 6c, is deployed to produce the holders 20, 21. As shown schematically in FIG. 6a, a blank 22 of the holder 20 made of a base material, for example a steel alloy, additionally for example chrome steel, is provided or manufactured first. Deviating from the preceding representations, the blank is schematically represented in a significantly simplified manner, since merely the method steps performed, but not the constructive configuration thereof, is to be explained.

The blank 22 has at least one fixing region 26 and a take-up region 24. Since a chrome steel is used, which has relatively poor solderability, the fixing region 26 is, however, still not suitable for fixing by means of a soldered connection.

FIG. 6b shows how the blank 22 is provided with a coating 23, e.g. a layer of gold. This happens, for example, as indicated in FIG. 6b, in a galvanic bath 70. In this process, a large part of the surface of the blank 22 and, therefore, also the fixing region 26 is coated with the coating 23. Due to the coating 23, the fixing region 26 has significantly improved solderability.

Following the coating, the take-up region 24 is machined with an ultrashort-pulse laser, as indicated in FIG. 6c. Thanks to the treatment with the laser beam 61, the coating 23 is removed and the chrome steel located thereunder in the take-up region 24 is blackened, so that reflections in this region are avoided. The coating 23 of the basic form 22 is indicated with vertical shading and the blackened take-up region 24 is indicated with continuous transversely running hatching.

In contrast to the method step of coating, the laser-assisted surface treatment is very precise in terms of the machined surface so that the removal and blackening are restricted precisely to the take-up region 24. In order to save costs and time during the laser-assisted surface treatment, both the removal and the blackening are performed with a single laser source 60. Both processes can even be performed in a single work step.

Figure 7:
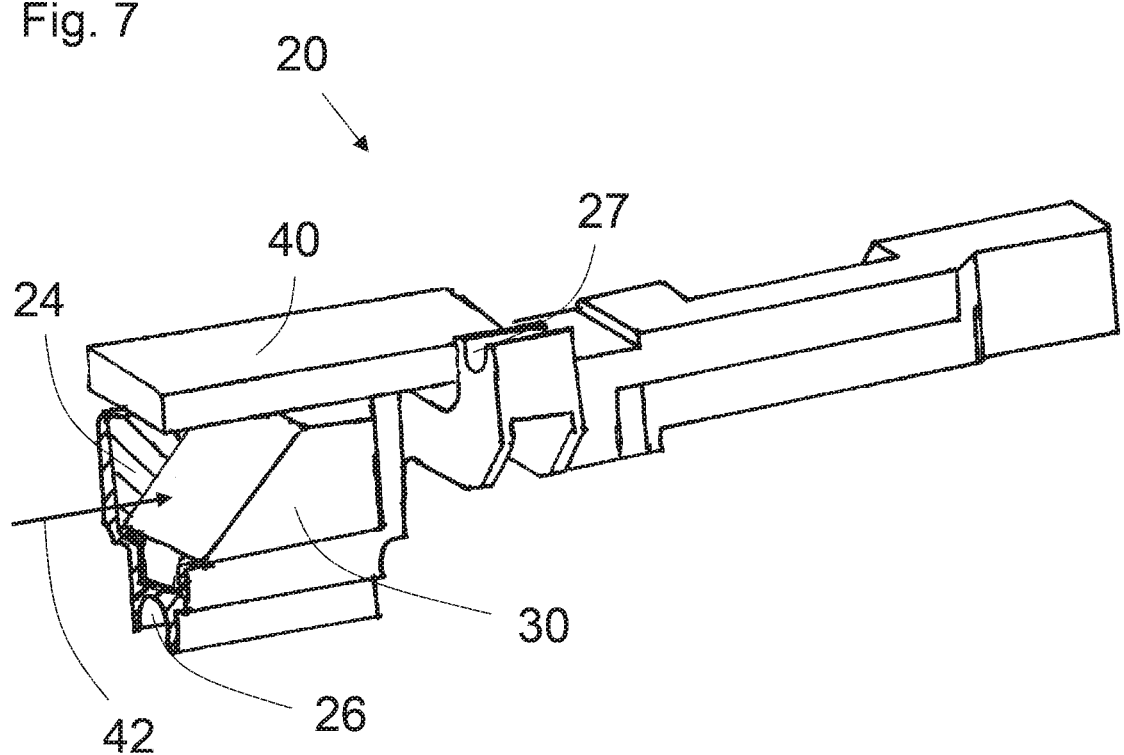
FIG. 7 illustrates a schematically simplified perspective representation of a holder for an optical system of an endoscope having a deflection prism and an image sensor.
Figure 8:
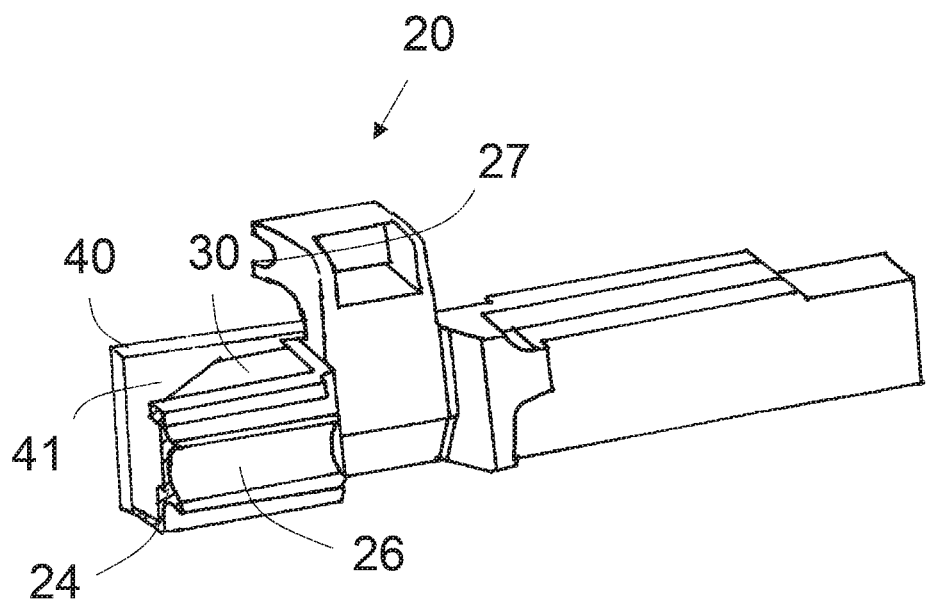
FIG. 8 illustrates shows a schematically simplified perspective representation of a holder for an optical system of an endoscope having a deflection prism and an image sensor in a view rotated about the longitudinal axis of the holder compared with the representation in FIG. 7.

In FIGS. 7 and 8, two different perspective views of the holder from FIG. 5 are shown, following the laser treatment, in a schematic and simplified manner. An optical element 30, by way of example a deflection prism, is deployed in the blackened take-up region 24 and fixed there, for example pasted therein. In addition, an image sensor 40 is arranged on the holder 20 such that light bundles incident from the direction of incident light 42 are diverted by the deflection prism in the direction of an active surface 41 of the image sensor 40. The direction of incident light 42 corresponds to one of the optical axes 53, 54 of the optical system 10 in the fixed condition of the holder 20.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
3 Shaft
4 Handle
10 Optical system
12 Distal optical assembly
14 Proximal optical assembly
15 First fixing element
16 Second fixing element
20 First holder
21 Second holder
22 Blank
23 Coating
24 Take-up region
26 First fixing region
27 Second fixing region
30 Optical element
40 Image sensor
41 Optically active surface
42 Direction of incident light
51 First lens system channel
52 Second lens system channel
53 First optical axis
54 Second optical axis
56 Longitudinal axis
60 Laser source
61 Laser beam
70 Galvanic bath
80 Printed circuit board

What is claimed is:

1. An optical system for use with an endoscope, the optical system comprising:
a distal optical assembly comprising at least one fixing member and one or more optical lenses; and
a proximal optical assembly comprising:
a prism; and
a holder comprising a holder body having an exterior surface, the exterior surface comprising:
a cavity having a bottom and one or more walls extending from the bottom, the prism being disposed in the cavity; and
at least one fixing surface configured to fix the holder body to the distal optical assembly by a soldered connection between the at least one fixing member and the at least one fixing surface, the at least one fixing surface being separate from the cavity;
wherein a material of the holder body is a base material that is provided with a coating, a material of the coating having better solderability than the base material, the coating being removed from the cavity to expose a surface of the cavity, the exposed surface being blackened by a laser-assisted surface treatment; and
the at least one fixing member is separately formed from the at least one fixing surface with the coating arranged between the at least one fixing member and the at least one fixing surface.

2. The optical system according to claim 1, wherein the base material is a steel alloy.

3. The optical system according to claim 2, wherein the steel alloy is a chrome steel.

4. The optical system according to claim 1, wherein the coating in the cavity is removed and the surface of the cavity is blackened by means of laser-assisted surface treatment with an ultrashort-pulse laser.

5. The optical system according to claim 1, wherein the proximal optical assembly further comprises an image sensor and the holder body is configured to receive the image sensor such that a light-sensitive sensor surface of the image sensor extends parallel to a direction of incident light, wherein light bundles incident along the direction of incident light into the prism are deflected in the direction of the received image sensor by the prism.

6. The optical system according to claim 1, wherein
the at least one fixing member is at least one elongated bar extending from the distal optical assembly; and
the at least one fixing surface comprises at least one elongated concavity for receiving the elongated bar, the at least one elongated concavity having the coating.

7. The optical system according to claim 6, wherein
the soldered connection comprises a first soldered connection and a second soldered connection;
the at least one elongated concavity comprises a first elongated concavity and a second elongated concavity, and
the at least one elongated bar comprises a first elongated bar connected to the first elongated concavity by the first soldered connection and a second elongated bar connected to the second elongated concavity by the second soldered connection.

8. The optical system according to claim 6, wherein
the optical system is configured for use in a stereo-video endoscope,
the one or more optical lenses of the distal optical assembly comprises a first lens system channel having a first optical axis and a second lens system channel having a second optical axis, the first optical axis runs parallel to the second optical axis,
the holder comprises a first holder and a second holder, a first prism is received in the cavity of the first holder and a second prism is received in the cavity of the second holder, such that light bundles guided along the first lens system channel are diverted by the first prism and light bundles guided along the second lens system channel are diverted by the second prism.

9. The optical system according to claim 8, wherein the first holder and the second holder are arranged symmetrically to one another in the optical system.

10. The optical system according to claim 9, wherein the first holder is arranged axisymmetrically to the second holder with respect to a longitudinal axis of the optical system and the longitudinal axis runs centrally between the first optical axis and the second optical axis.

11. An endoscope comprising the optical system according to claim 6.

12. A method for manufacturing an optical system for use with an endoscope, the method comprising:
providing a distal optical assembly having a fixing member and one or more optical lenses;
providing a blank of a holder made from a base material;
subsequent to the providing of the blank, coating an exterior surface of the blank with a coating, the coating having better solderability than the base material, wherein the coated blank having a fixing surface for fixing the coated blank to the distal optical system, the fixing surface is provided on the exterior surface of the coated blank;
subsequent to the coating, treating a cavity on the exterior surface of the coated blank with a laser treatment to remove the coating in the cavity and blacken the surface of the cavity by the laser treatment, the cavity having a bottom and one or more walls extending from the bottom;
subsequent to the laser treatment, disposing a prism in the cavity, wherein the cavity is separate from the fixing surface; and
soldering the fixing member to the fixing surface to form a soldered connection between the distal optical assembly and the holder.

13. The method according to claim 12, wherein the laser treatment of the cavity is effected with an ultrashort-pulse laser.

14. The method according to claim 13, wherein the removal of the coating in the cavity and the blackening of the cavity are effected with a single laser source, and the removal of the coating in the cavity and the blackening of the cavity are performed in a single step.

15. The optical system according to claim 1, wherein
the soldered connection comprising a first soldered connection and a second soldered connection;
the at least one fixing member of the distal optical assembly comprising a first fixing member and a second fixing member, the first fixing member and the second fixing member separably extending from the distal optical assembly;
the at least one fixing surface comprising a first fixing surface and a second fixing surface to fix the holder body to the distal optical system by the first soldered connection between the first fixing member and the first fixing surface and the second optical connection between the second fixing member and the second fixing surface, the second fixing surface being non-continuously formed with the first fixing surface.

16. The optical system according to claim 15, wherein
the first fixing member and the second fixing member comprise a first elongated bar and a second elongated bar, respectively, each separately extending from the distal optical assembly;
the first fixing surface and the second fixing surface comprises a first elongated concavity and a second elongated concavity, respectively, for respectively receiving the first elongated bar and the second elongated bar; and
each of the first elongated concavity and the second elongated concavity having the coating.

17. The optical system according to claim 1, wherein
the holder having the cavity at one end thereof and an elongated body extending from the one end to another end; and
the at least one fixing surface is provided adjacent to the bottom of the cavity.

18. The optical system according to claim 1, wherein
the holder having the cavity at one end thereof and an elongated body extending from the one end to another end; and
the at least one fixing surface is provided at the elongated body.

19. The optical system according to claim 15, wherein
the holder having the cavity at one end thereof and an elongated body extending from the one end to another end;
the first fixing surface is provided adjacent to the bottom of the cavity; and
the second fixing surface is provided at the elongated body.

20. The optical system according to claim 15, wherein the first fixing member and the second fixing member are disposed on a face of the distal optical assembly with the one or more optical lenses disposed therebetween in a radial direction of the face.

\* \* \* \* \*